United States Patent [19]

Larson

[11] Patent Number: 5,175,179
[45] Date of Patent: Dec. 29, 1992

[54] METHOD FOR TREATING HYPERTENSION

[75] Inventor: Eric R. Larson, Groton, Conn.

[73] Assignee: Pfizer Inc., New York, N.Y.

[21] Appl. No.: 765,643

[22] Filed: Sep. 25, 1991

[51] Int. Cl.⁵ .............................................. A61K 31/425
[52] U.S. Cl. .................................... 514/369; 514/929
[58] Field of Search ................................ 514/369, 929

[56] References Cited

U.S. PATENT DOCUMENTS 5,036,079  7/1991  Clark et al. .......................... 514/333
5,053,420  10/1991  Singh .................................... 514/369

FOREIGN PATENT DOCUMENTS 9105538  5/1991  PCT Int'l Appl. .
9112003  8/1991  PCT Int'l Appl. .

OTHER PUBLICATIONS

Kaplan, Clinical Diabetes, 9, 1–9 (1991).
Ferranninni, et al., New England Journal of Medicine, 315, 350–57 (1987).
Shen, et al., Journal of Clinical Endocrinology and Metabolism, 66, 580–83 (1988).

Primary Examiner—Frederick E. Waddell
Assistant Examiner—Kimberly Jordan
Attorney, Agent, or Firm—Peter C. Richardson; J. Trevor Lumb; Robert T. Ronau

[57] ABSTRACT

A method of using certain thiazolidine-2,4-diones in the treatment of hypertension.

4 Claims, No Drawings

METHOD FOR TREATING HYPERTENSION

BACKGROUND OF THE INVENTION

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other sign of disease or disorder.

It is known that hypertension can directly lead to heart failure, renal failure and stroke (brain hemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of β-blockers, vasoconstrictors, renin inhibitors and the like have been developed and marketed as antihypertensives. The treatment of hypertension utilizing these compounds has proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. (See, for example, Kaplan, N.M., Clinical Diabetes, 9, 1-9 (1991), Ferranninni, E., et. al., New England Journal of Medicine, 317. 350-57 (1987), and Shen, D.-C., Journal of Clinical Endocrinology, 66, 580-3 (1988).) Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries; while sodium retention increases blood volume. Thus, the lowering of insulin levels in hyperinsulinemics can prevent abnormal vascular growth and renal sodium retention caused by high insulin levels and thereby should alleviate hypertension.

Pershadsingh, et al., International Patent Publication No. WO 91/05538, disclose the following antihypertensive thiazolidinediones:

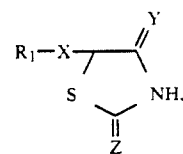

where X is a lower alkylidene or a bond; or —HC=CH—; Y is oxo or imino; Z is oxo or imino; and $R_1$ is a structurally diverse variable comprised of such groups as

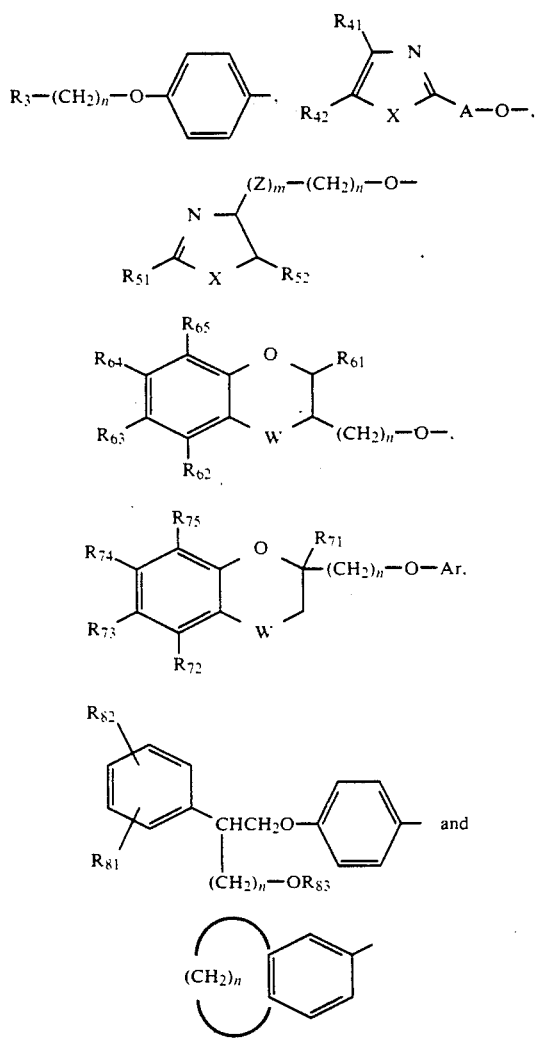

with definitions of the remaining variables given in detail in said patent application.

The present invention is directed to a new use for the compounds of formula (I),

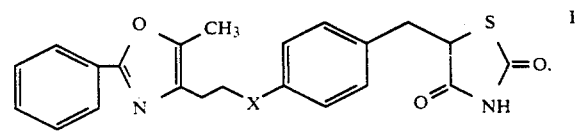

wherein X is C=O or CHOH. These compounds have been disclosed in U.S. Pat. No. 5,036,079 as being useful in the treatment of hyperglycemia and hypercholesterolemia, by virtue of blood glucose level lowering properties and blood cholesterol level lowering properties, respectively.

The present invention provides the surprising and beneficial result that these compounds lower plasma insulin levels after administration to a mammalian subject. More particularly, this insulin level lowering effect is independent of the hypoglycemic properties of the compounds of formula (I). Thus, the compounds of formula (I) reduce insulin levels in a hyperinsulinemic, normoglycemic patient without affecting the blood glucose levels in said patient. The term "normoglycemic patient" is defined as a patient having normal glucose levels. This lowering of blood insulin levels results in a reduction of blood pressure in a hypertensive mammal.

The new use of the present invention comprises administration of at least one of the foregoing compounds of formula I to a mammal suffering from hypertension. Said compounds lower blood insulin levels of the suffering mammal thereby alleviating the hypertension.

SUMMARY OF THE INVENTION

The present invention is directed to a method of reducing blood pressure in a hypertensive mammal which comprises administering to said mammal a blood pressure lowering effective amount of a compound of formula (I).

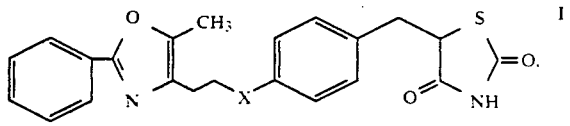

or a pharmaceutically acceptable salt thereof, wherein X is —C=O or —CHOH.

DETAILED DESCRIPTION OF THE INVENTION

The compounds of formula (I),

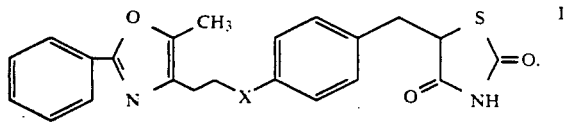

wherein X is C=O or CHOH, pharmaceutically acceptable cationic salts thereof, pharmaceutically acceptable acid addition salts thereof and the preparation thereof are described in U.S. Pat. No. 5,036,079, the teachings of which are incorporated herein by reference.

The present invention is directed to a new use for the compounds of formula (I) and their pharmaceutically acceptable salts which comprises a method of treatment of hypertension in a hypertensive mammal with elevated insulin levels comprising treating said mammal with a blood pressure lowering effective amount of said compounds. A blood pressure lowering effective amount of a compound of formula (I) effects reduction in blood pressure by returning blood insulin levels to a normal value. Thus a blood pressure lowering effective amount of a compound of formula (I) is equivalent to a blood insulin level lowering effective amount of a compound of formula (I).

Also within the scope of the present invention are the methods of treatment wherein the optically pure forms of the compounds of formula (I) wherein X is CHOH are utilized. Thus, the methods of use of the following compounds are embraced by the present invention:

a) the compound of formula (I) wherein X is CHOH and the carbon atom of X has the (R) configuration, the compound being substantially free from the enantiomer in which the carbon atom of X has the (S) configuration;

b) the compound of formula (I) wherein X is CHOH and the carbon atom of X has the (S) configuration, the compound being substantially free from the enantiomer in which the carbon atom of X has the (R) configuration.

The two optically active enantiomers of the compound of formula (I) are prepared by resolution of the racemic mixture or by enantioselective reduction of the ketone precursor (II).

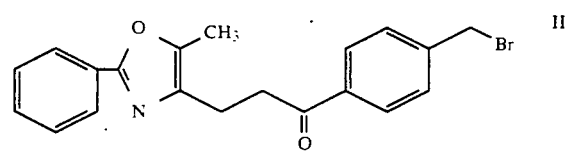

The racemic mixture is resolved into its individual optically pure components by reaction with a chiral isocyanate, said chiral isocyanate being chosen for its ability to produce diastereoisomers which are easily separable by some physical means. Thus, (R)-(-)-1-(naphthyl)ethylisocyanate is reacted with the racemic alcohol in refluxing toluene for 17 hours. An additional amount of isocyanate is added, in order to drive the reaction to completion, and reflux is continued for 24 hours. The reaction yields two diastereomeric carbamates of the configurations RR and RS. The differing physical properties of these diastereomers results in one, the RR isomer, being selectively crystallized from a solution containing equal amounts of the two compounds. The solution used in this particular instance is a diethyl ether/hexane (½) system. The solid material obtained from this crystallization is recrystallized from ethyl acetate to further purify the (RR)-diastereomer.

The mother liquors of the crystallization and recrystallization steps now predominantly contain the (RS)-diastereomer. Removal of the solvents and purification of the residue on silica gel, eluting with hexane/diethyl ether (¼) affords the optically pure (RS)-diastereomer.

The diastereomers thus separated are now converted back to the alcohols from the carbamates by reaction of said carbamates with trichlorosilane and triethylamine in benzene. Each of the alcohols thus obtained exist as one enantiomer, substantially free of its corresponding enantiomer.

The enantioselective reduction is achieved with a borane reducing agent such as borane methyl sulfide complex, catecholborane or borane tetrahydrofuran in the presence of the appropriate chiral oxazaborolidine catalyst in a cyclic ether solvent such as dioxane or tetrahydrofuran. The choice of the stereochemistry of the catalyst directly influences the stereochemical configuration of the product alcohol. Thus, the choice of an R-configured catalyst results in the S-configured alcohol; the choice of an S-configured catalyst results in the R-configured alcohol. Specifically, the preferred system to produce the S-alcohol is reaction of the ketone of formula (II) with borane methyl sulfide complex in tetrahydrofuran in the presence of (R)-tetrahydro-1-methyl-3, 3-diphenyl-1H,3H-pyrrolo[1,2-c]-[1,3,2]pxaza-borole at room temperature for about 15 minutes to 3 hours; the preferred system to produce the R-alcohol is reaction of the ketone of formula (II) with borane methyl sulfide complex in tetrahydrofuran in the presence of (S)-tetrahydro-1-methyl-3,3-diphenyl-1H,3H-pyrrolo [1,2-c]-[1,3,2]oxazaborole.

The alcohols obtained in this fashion are further elaborated to the thiazolidinedione derivatives using straightforward organic chemistry as described below.

The R alcohol is reacted with t-butyldimethylsilyl-chloride and imidazole in dimethylformamide at room temperature overnight to afford the O-protected alcohol. With the alcohol moiety thus protected, the bromide is converted to an aldehyde using the well-known conditions of n-butyllithium at −78° C., cold quenching of the anion with dry dimethylformamide and standard aqueous workup. Standard aqueous workup is defined as diluting the reaction mixture with water and extraction of the resulting aqueous solution with enough organic solvent, usually two or three portions, to remove any organic compounds from the aqueous solution. The organic solvent, generally ethyl acetate, is then removed in vacuo.

The aldehyde thus obtained is condensed with commercially available 2,4-thiazolidinedione using the conventional methods of refluxing ethanol and piperidine catalysis, to obtain the olefin condensation product. The olefin thus generated is hydrogenated by introducing hydrogen into a sealed reaction vessel containing the olefin, a reaction inert solvent and a catalyst. The pressure inside the reaction vessel can vary from 15 to 50 PSI. Hydrogenation will occur within about 2 to 48 hours under these conditions. The preferred catalyst is palladium due to its resistance to poisoning by sulfur; and the palladium is supported on an inert substrate such as carbon. By "reaction inert solvent" is meant a solvent which will not decompose or otherwise interfere with the reaction. Reaction inert solvents for reactions of this type include ethanol, methanol and tetrahydrofuran but are not limited to these solvents. The preferred solvent in this case is tetrahydrofuran.

The protecting group is removed using 3.5% aqueous perchloric acid in tetrahydrofuran at room temperature for about 12 hours. This provides the R alcohol of formula (III).

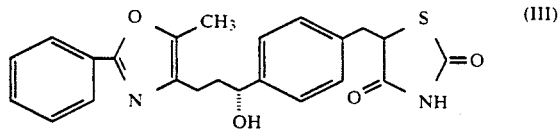

The corresponding S alcohol can be prepared by utilizing the same route, but starting with the S enantiomer obtained by the enantioselective reduction step.

As disclosed in the U. S. Pat. No. 5,036,079, the compounds of formula (I) are basic and are capable of forming acid addition salts. All such salts are within the scope of this invention and can be prepared as taught by said patent. The expression "pharmaceutically acceptable acid addition salts" is intended to define but not limited to such salts as hydrocholoride, hydrobromide, sulfate, hydrogen sulfate, phosphate, hydrogen phosphate, dihydrogen phosphate, acetate, succinate, citrate, methanesulfonate (mesylate) and p-toluenesulfonate (tosylate) salts.

As disclosed in the U.S. Pat. No. 5,036,079, the compounds of formula (I) are also acidic and are thus capable of forming cationic salts. All such salts are within the scope of this invention and can be prepared as taught by said patent. The expression "pharmaceutically acceptable cationic salts" is intended to define but not limited to such salts as the alkali metal salts (e.g. sodium and potassium), alkaline earth metal salts (e.g. calcium and magnesium), aluminum salts, ammonium salts and salts with organic amines such as benzathine (N, N'-dibenzylethylenediamine), choline, diethanolamine, ethylenediamine, benethamine (N-benzylphenylethylamine), diethylamine, tromethamine (2-amino-2-hydroxy-methyl-1,3-propanediol) and procaine. An especially preferred such salt is the sodium salt.

The method of this invention comprises administering a compound of formula (I) or a pharmaceutically acceptable salt thereof to a mammal. Said compound can be administered alone, or preferably, in combination with pharmaceutically acceptable carriers or diluents in a pharmaceutical composition, according to standard pharmaceutical practice. Such administration can be oral or parenteral.

Generally, in a human subject, oral administration of these compounds is the preferred route, being more convenient and avoiding the possible pain and irritation of an injection. In circumstances where the patient cannot swallow the medication, or absorption following oral administration is impaired, as by disease or other abnormality, it is essential that the drug is administered parenterally. Parenteral administration as used herein includes, but is not limited to, intravenous, intramuscular, intraperitoneal or subcutaneous. When the parenteral route is chosen, intramuscular administration is the preferred vehicle in man.

In a human, by either the oral or parenteral route, the dosage is in the range of about 0.10 to about 50 mg/kg body weight of the subject per day, preferably about 0.10 to about 10 mg/kg body weight per day administered singly or as divided dose. However, the optimum dosage for the individual subject being treated will be determined by the person responsible for treatment, generally smaller doses being administered initially and thereafter increments made to determine the most suitable dosage. This will vary according to which of the compounds is employed and with the subject being treated.

For the purposes of oral administration the compounds can be combined with a suitable solid or liquid carrier to form capsules, tablets, powders, syrups, solutions, suspensions and the like. The pharmaceutical compositions may, if desired, contain additional components such as flavorants, sweeteners, excipients and the like.

For the purpose of parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts or cationic salts of the compounds. The injectable solutions prepared in this manner can then be administered by one of the parenteral routes recited above, if so desired.

The ability of the compounds of the invention to lower plasma insulin levels is demonstrated by the assay procedure described hereinbelow. Male C57BL/6J-ob/ob mice, their lean littermates (ob/+or ob/?) and C57BL/Ks-db/db mice are supplied at 5-6 weeks of age by Jackson Laboratories (Bar Harbor, Maine) and fed standard rodent diet (Prolab R-M-H 3000 from Agway R, Syracuse, NY) ad libitum. Said mice are allowed to acclimatize for at least 5 days before the studies begin. Male Sprague Dawley rats, 140-160 g, are supplied by Charles River (Kingston, NY), and are fed standard rodent diet (Prolab R-M-H 3000 from Agway R, Syracuse NY) ad libitum. The rats are allowed to acclimatize for at least 7 days before the studies begin. The drug is administered as a 0.25% solution (weight/volume) in methyl/cellulose by oral gavage. A single daily dose is maintained for 1 to 11days. Each drug is administered as the sodium salt. (Dosasges, however, are expressed as the amount of free acid administered daily). Twenty-four hours after the last dose is administered, blood is collected (25 or 50 μl) by capillary pipette from the retro-orbital sinus of ob/ob mice or the tail vein of rats. Said blood is collected for the determination of insulin level. The blood is diluted in 100 μl of heparinized saline or 150 μl of heparinized saline containing 1% (weight/volume) of bovine serum albumin. The solution thus prepared is centrifuged and the supernatant is assayed for insulin. Plasma concentrations in diluted blood samples are calculated assuming a 44% hematocrit. Insulin radioimmunoassay kits were purchased from Cambridge Diagnostics, Billerica, MA. The interassay coefficient of variation was ≦10%.

Claims

1. A method of lowering blood pressure in a mammal suffering from hypertension which comprises administering to said mammal a blood pressure lowering effective amount of a compound of formula (I),

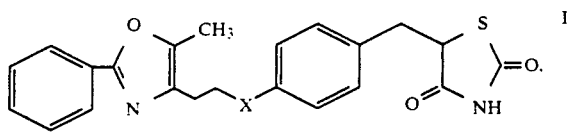

wherein X is C=O or CHOH; a pharmaceutically acceptable cationic salt thereof or a pharmaceutically acceptable acid addition salt thereof.

2. The method according to claim 1 wherein X is C=O.

3. The method according to claim 1 wherein X is CHOH and the carbon atom of X has the (R) configuration, the compound being substantially free from the corresponding enantiomer in which the carbon atom of X has the (S) configuration.

4. The method according to claim 1 wherein X is CHOH and the carbon atom of X has the (S) configuration, the compound being substantially free from the corresponding enantiomer in which the carbon atom of X has the (R) configuration.

* * * * *